United States Patent
Blaschke et al.

(10) Patent No.: US 6,972,345 B2
(45) Date of Patent: Dec. 6, 2005

(54) EXTRACTION OF PHENOL-CONTAINING EFFLUENT STREAMS

(75) Inventors: Ulrich Blaschke, Krefeld (DE); Stefan Westernacher, Kempen (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/108,237

(22) Filed: Apr. 18, 2005

(65) Prior Publication Data

US 2005/0240065 A1    Oct. 27, 2005

(30) Foreign Application Priority Data

Apr. 24, 2004  (DE)  ............ 10 2004 020 113

(51) Int. Cl.$^7$ .............................. C07C 39/16
(52) U.S. Cl. ............ 568/728; 568/749; 210/634
(58) Field of Search ............ 568/728, 749; 210/634

(56) References Cited

U.S. PATENT DOCUMENTS 4,400,553 A * 8/1983 Aneja ................ 568/724
5,716,524 A * 2/1998 Stonner et al. ........ 210/634

OTHER PUBLICATIONS

Chemistry Data Series, vol. V, Part 1, (month unavailable) 1979, pp. 356-361, J.M. Sørensen and W. Arit, "Liquid-Liquid Equlibrium Data Collection".
Ullmann's Encyclopedia of Industrial Chemistry, vol. A 19, 5$^{th}$ edition, (month unavailable) 1991, pp. 299-312, Wilfried Jordan et al, "Phenol".

* cited by examiner

Primary Examiner—Michael L. Shippen
(74) Attorney, Agent, or Firm—Joseph C. Gil; Aron Preis

(57) ABSTRACT

A process for extracting phenol from a phenol-containing aqueous solution is disclosed. The process entails contacting the aqueous solution with an extracting agent that comprise a mixture of 60 to 99% of methyl isobutyl ketone, 1 to 40% of anisole and 0 to 20% of mesitylene.

10 Claims, No Drawings

EXTRACTION OF PHENOL-CONTAINING EFFLUENT STREAMS

FIELD OF THE INVENTION

The invention relates to chemical extraction and particularly to extracting phenol-containing effluent streams.

BACKGROUND OF THE INVENTION

In industrial processes such as, for example, the production of phenol by the cumene process or the production of bisphenol A by the condensation of phenol and acetone, phenol-containing aqueous solutions are produced as effluent streams.

The separation of phenol from such effluent streams is not possible using a simple distillation process due to the solubility of phenol in water (the two substances are fully miscible with each other at temperatures above 65.3° C., and almost 10 wt. % of phenol still dissolves in water at room temperature) and the formation of azeotropic mixtures during distillation of such solutions (J. M. Sørensen, W. Arlt, Liquid—Liquid Equilibrium Data Collection, Chemistry Data Series V/1, p. 356–361, Dechema, Frankfurt 1979; Ullmann's Encyclopedia of Industrial Chemistry, vol. A 19, p. 299–312, 5th edition, VCH Weinheim 1991).

When preparing bisphenol A with the aid of acid ion exchangers, the water formed in the reaction has to be removed because otherwise the activity of the catalyst is reduced. This is achieved in the first instance by isolating the water of reaction from the bisphenol A, its isomers and the phenol used in excess as solvent in the bisphenol-A process by distillation. The water obtained by this type of distillation contains a lot of phenol (1–15 wt. % phenol) and optionally also contains acetone (0–5 wt. %). In addition to these two main contaminants, other organic components such as methanol, acetone self-condensation products, such as for example mesityl oxide, the sulfur-containing co catalyst (a thiol) used in the bisphenol A process as well as degradation and secondary products of these compounds may also be present in the separated water. However, other aqueous streams which are produced in such a process may also contain phenol, as well as other organic components (e.g. water for floating ring seals or vacuum equipment).

Due to the toxicity of phenol and also for economic reasons (recovery of phenol), the phenol-containing effluent is purified in an extraction process using an organic solvent. Benzene, cumene, diisopropyl ether or methyl isobutyl ketone (MIBK), for example, are used for this purpose. The extraction may be performed using any technique known to a person skilled in the art (tank extractors, mixer-settler systems, counterstream extraction, etc.). In a subsequent step, the effluent treated in this way is generally processed on a steam stripping column in order to lower the residual concentration of extraction agent. This is important because residual concentrations of extraction agents lead to heavy organic pollution of the effluent. By reducing the concentration of extraction agent in the effluent, the use of steam, and thus energy costs, can be saved. The effluent treated in this way is then subjected to biological effluent treatment in an effluent treatment plant.

SUMMARY OF THE INVENTION

A process for extracting phenol from a phenol-containing aqueous solution is disclosed. The process entails contacting the aqueous solution with an extracting agent that comprise a mixture of 60 to 99% of methyl isobutyl ketone, 1 to 40% of anisole and 0 to 20% of mesitylene.

DETAILED DESCRIPTION OF THE INVENTION

It has now been found that, when extracting phenol-containing aqueous solutions with MIBK as the extraction agent, the residual concentration of MIBK after extraction may be reduced when the MIBK used for extraction also contains some anisole and optionally mesitylene.

The invention provides a process for extracting phenol-containing aqueous solutions in which a mixture containing 60 to 99 wt. % of methyl isobutyl ketone, 1 to 40 wt. % of anisole and 0 to 20 wt. % of mesitylene, with respect to the mixture, is used as extraction agent.

A process for extracting phenol-containing aqueous solutions in which a mixture containing 75 to 95 wt. % of methyl isobutyl ketone, 5 to 25 wt. % of anisole and 0 to 10 wt. % of mesitylene, with respect to the mixture, is used as extraction agent, is preferred.

By extracting a phenol- and acetone-containing effluent with a mixture of MIBK and anisole instead of pure MIBK, the residual concentration of MIBK in the effluent is greatly reduced, given the same conditions of extraction. The degree of extraction for phenol and acetone remains virtually the same.

Although, when using a mixture of MIBK and anisole, small amounts of anisole are found in the effluent, the decrease in MIBK concentration is much greater than the increase in concentration of anisole so that overall an effluent with a lower concentration of organic constituents is obtained. By adding mesitylene to the extraction mixture, the concentration of anisole in the water after extraction can be further reduced while retaining the same extraction effect and residual concentration of MIBK.

The phenol concentration in the aqueous solution (the effluent) is preferably 1 to 15 wt. %, with respect to the aqueous solution.

In addition, up to 5 wt. % of acetone, with respect to the aqueous solution, may also be present.

To improve the extraction process, the aqueous solution may also contain sodium sulfate and/or the aqueous solution may be acidified to a pH<7, e.g. using sulfuric acid or other acids.

The extraction may be performed using any technique known to a person skilled in the art (multi-stage extraction, tank extractors, mixer-settler systems, counterstream extraction, etc.).

After extraction, residues of the extraction agent may also be removed from the effluent by distillation in a column, optionally while supplying steam.

The aqueous phase obtained after distillation or extraction may also be taken for treatment in a biological effluent treatment plant.

The phenol-containing aqueous solution may also be subjected to a distillation process before extraction, during which for example, any ketones or other organic components which are present are entirely or partly removed.

The phenol and optionally other extracted organic components (in particular optionally extracted acetone) extracted from the phenol-containing aqueous solution may be separated from the extraction agent by distillation and thus recovered. The extraction agent which is purified in this way may be used again in the extraction process.

The aqueous phase obtained after extraction or after distillation may also be purified with activated carbon prior to treatment in a biological effluent treatment plant.

The process according to the invention is preferably used for the purification of effluents from the production of bisphenol A. In the process for the production of bisphenol A, for example, phenol and acetone are reacted on sulfonic acid cation exchangers as catalyst, optionally in the presence of a thiol as co catalyst, the bisphenol A obtained is entirely or partly crystallized out in the form of bisphenol A-phenol adduct crystals and filtered off and then water is removed from the filtrate, entirely or partly, by distillation. Likewise it may be used in a process for the production of bisphenol A in which separation of the water of reaction takes place, differently from the process described above, entirely or partly prior to crystallization of the bisphenol A-phenol adduct crystals. In addition, it is suitable for the extraction of effluents from a process for the production of bisphenol A in which water (optionally mixed with phenol or with other organic solvents) is added during or before the crystallization step.

EXAMPLES

Example 1 (Comparison Example)

170 ml of a phenol-containing aqueous solution (process effluent from the production of bisphenol A) is shaken with 100 ml of MIBK for 15 seconds in a 500 ml separating funnel. The separating funnel is then allowed to stand for 5 minutes, the aqueous phase can be drained off and this phase is tested using gas chromatography. The results are given in table 1.

Example 2 (According to the Invention)

Example 2 is performed in the same way as example 1, with the difference that a mixture of 80 ml of MIBK and 20 ml of anisole is used instead of 100 ml of MIBK. The results are given in table 1.

Example 3 (According to the Invention)

Example 3 is performed in the same way as example 1, with the difference that a mixture of 83 ml of MIBK, 12 ml of anisole and 5 ml of mesitylene is used instead of 100 ml of MIBK. The results are given in table 1.

TABLE 1

Results of extraction trials (wt. % in the aqueous phase after extraction)

| Compound | Example 1 | Example 2 | Example 3 |
|---|---|---|---|
| Phenol | 0.21 | 0.23 | 0.25 |
| MIBK | 1.40 | 1.00 | 1.05 |
| Acetone | 0.017 | 0.015 | 0.017 |
| Anisole | <0.005 | 0.044 | 0.025 |
| Mesitylene | <0.005 | <0.005 | <0.005 |
| Total | approx. 1.63 | approx. 1.29 | approx. 1.35 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for extracting phenol from a phenol-containing aqueous solution comprising contacting the aqueous solution with an extracting agent comprising a mixture of 60 to 99% of methyl isobutyl ketone, 1 to 40% of anisole and 0 to 20% of mesitylene, the % all occurrences being relative to the weight of the mixture.

2. The process according to claim 1, in which the phenol concentration in the phenol-containing aqueous solution is 1–15% relative to the weight of the solution.

3. The process according to claim 1 in which the phenol-containing aqueous solution is at least partially derived from the production of bisphenol A.

4. The process according to claim 1 in which the phenol-containing aqueous solution contains sodium sulfate.

5. The process according to claim 1 in which the solution further contains acetone in an amount of up to 5% relative to the weight of the solution.

6. A process for extracting phenol from a phenol-and-acetone containing aqueous solution wherein acetone content is a positive amount of up to 5% relative to the weight of the solution comprising distilling the solution to separate at least some of the acetone to obtain a distilled solution and contacting the distilled solution with an extracting agent comprising a mixture of 60 to 99% relative to the weight of the mixture of methyl isobutyl ketone, 1 to 40% relative to the weight of the mixture of anisole and 0 to 20% relative to the weight of the mixture of mesitylene.

7. A process for extracting phenol from a phenol-containing aqueous solution comprising:
   (i) contacting the aqueous solution with an extracting agent to obtain phenol and a material system that contains methyl isobutyl ketone, and
   (ii) distilling the material system to obtain an aqueous solution wherein concentration of methyl isobutyl ketone is lower than that in the material system, said extracting agent comprising a mixture of 60 to 99% of methyl isobutyl ketone, 1 to 40% of anisole and 0 to 20% of mesitylene, the % all occurrences being relative to the weight of the mixture.

8. A process for extracting phenol from a phenol-and-acetone-containing aqueous solution wherein acetone content is a positive amount of up to 5% relative to the weight of the solution comprising
   (i) distilling the solution to separate at least some of the acetone to obtain a distilled solution
   (ii) contacting the distilled solution with an extracting agent to obtain phenol and a material system that contains methyl isobutyl ketone, and
   (iii) distilling the material system to obtain an aqueous solution wherein concentration of methyl isobutyl ketone is lower than that in the material system, said extracting agent comprising a mixture of 60 to 99% relative to the weight the mixture of methyl isobutyl ketone, 1 to 40% relative to the weight of the mixture of anisole and 0 to 20% relative to the weight of the mixture of mesitylene.

9. A process for extracting phenol from a phenol-containing aqueous solution comprising contacting the aqueous solution with an extracting agent to obtain material system containing phenol and methyl isobutyl ketone and distilling the material system to obtain phenol, said extracting agent comprising a mixture of 60 to 99% of methyl isobutyl ketone, 1 to 40% of anisole and 0 to 20% of mesitylene, the % all occurrences being relative to the weight of the mixture.

10. A process for extracting phenol from a phenol-containing aqueous solution comprising acidifying said solution to a pH lower than 7 to obtain an acidified solution and contacting the acidified solution with an extracting agent comprising a mixture of 60 to 99% of methyl isobutyl ketone, 1 to 40% of anisole and 0 to 20% of mesitylene, the % all occurrences being relative to the weight of the mixture.

* * * * *